US 6,586,885 B2

United States Patent
Coll et al.

(10) Patent No.: US 6,586,885 B2
(45) Date of Patent: Jul. 1, 2003

(54) MHCD AND MICROFLUIDIC APPARATUS AND METHOD

(75) Inventors: Bernard F. Coll, Fountain Hills, CA (US); Frederic Zenhausern, Fountain Hills, AZ (US); Jeremy W. Burdon, Scottsdale, AZ (US); Chowdary R. Koripella, Scottsdale, AZ (US)

(73) Assignee: Motorola, Inc., Schaumburg, IL (US)

( * ) Notice: Subject to any disclaimer, the term of this patent is extended or adjusted under 35 U.S.C. 154(b) by 177 days.

(21) Appl. No.: 09/932,913

(22) Filed: Aug. 20, 2001

(65) Prior Publication Data

US 2003/0034740 A1 Feb. 20, 2003

(51) Int. Cl.[7] .............................................. H05B 31/26
(52) U.S. Cl. ............................ 315/111.21; 315/111.41; 250/307; 257/21.575; 216/41
(58) Field of Search ...................... 361/18; 315/111.21, 315/111.41; 356/501, 502; 257/21.575; 250/306, 307, 309, 310, 311; 216/41, 49

(56) References Cited

U.S. PATENT DOCUMENTS

| 4,274,063 | A |   | 6/1981  | Javan |
|-----------|---|---|---------|-------|
| 5,623,338 | A | * | 4/1997  | Wickramasinghe et al. .. 356/501 |
| 5,817,242 | A | * | 10/1998 | Biebuyck et al. ....... 438/745 X |
| 6,136,212 | A | * | 10/2000 | Mastrangelo et al. ......... 216/49 |
| 6,180,239 | B1| * | 1/2001  | Whitesides et al. ..... 257/21.575 |

FOREIGN PATENT DOCUMENTS

| DE | 19941270 C1 | 6/2001 |
| EP | 0231639 A2  | 8/1987 |
| EP | 0469733 A2  | 2/1992 |

OTHER PUBLICATIONS

Vojak et al., "Multistage, monolithic ceramic microdischarge device having an active length of ~0.27mm" Applied Physics Letters, vol. 78, No. 10, Mar. 5, 2001, pp. 1342.

* cited by examiner

Primary Examiner—Jessica Han
(74) Attorney, Agent, or Firm—William E. Koch

(57) ABSTRACT

A microhollow cathode discharge (MHCD) cavity and microfluidic channel are combined for interrogation of samples. The apparatus includes a dielectric body and layers of conductive material defining a MHCD cavity containing an environment for carrying a gas discharge within the MHCD cavity. The gas discharge generates gas based electromagnetic waves. Electrical connections apply a cathode discharge potential to the layers of conductive material. A microfluidic channel is integrated on the substrate, and a path extends from the MHCD cavity laterally through a portion of the microfluidic channel. A detector, which may be integrated on the common substrate, is positioned to receive electromagnetic waves from the path and electronic circuitry is coupled to the detector for acquiring and processing data.

52 Claims, 2 Drawing Sheets

30

30

MHCD AND MICROFLUIDIC APPARATUS AND METHOD

FIELD OF THE INVENTION

This invention relates to microhollow cathode discharge devices and to microfluidic devices and more particularly to structures and methods of integrating the devices.

BACKGROUND OF THE INVENTION

In gas and liquid sample analysis, capillary electrophoresis, blood chemistry analysis and analytical chemistry, smaller dimensions of capillaries often provide improved performances in throughput, speed, and reduced production or analysis costs (e.g. less reagents, smaller sample size, etc.). More recently, miniaturized planar separation systems (e.g. total microanalysis systems or lab-on-a-chip) have been fabricated by micromachining or microlithographic techniques in silicon, glass, and plastics. See for example Harrison D. J. et al., *Science*, 1993, 261, 895.

Although many separation systems have been demonstrated on-chip, there are only a few approaches to having on-chip optical detection systems reported into the literature. To date, epifluorescence detection external to a chip is commonly used for large channels of a few hundreds of microns in cross-section but there are needs for more sensitive optical detectors capable of measuring the passage of a small number of molecules in narrower channels. There are advantages to develop techniques to form channels with dimensions possibly smaller than the persistence length of a DNA polymer in order to extend the molecular strand to map its sequence. Single molecule manipulation will require high spatial resolution near-field optical probes requiring to go to some form of non-propagating evanescent mode. See for example, U.S. Pat. No. 5,623,339, entitled "Interferometric Measuring Method Based on Multiple Sensing" and U.S. Pat. No. 5,623,338, entitled "Interferometric Near-Field Apparatus Based on Multiple Sensing", incorporated herein by reference. Although narrow apertures can be easily formed in various evaporated metallic films on a transparent substrate combined with a microchannel, it is very challenging to place a light source directly on-chip.

Accordingly it is highly desirable to provide new and improved integrated microhollow cathode discharge, for example as a light source, and microfluidic devices and methods of fabrication

BRIEF DESCRIPTION OF THE DRAWINGS

Referring to the drawings.

DESCRIPTION OF THE PREFERRED EMBODIMENTS

The present invention pertains to a microhollow cathode discharge device in combination with a microfluidic channel for interrogating at least one physico-chemical property of various samples and preferably bio-samples, such as cells, bacteria, viruses, nucleic acids (e.g. DNA, RNA), proteins, lipids, carbohydrates, etc. Some typical examples of physico-chemical properties which may be interrogated in this fashion are: interactions between electromagnetic radiation and a workpiece (common interactions include refraction, reflection, or absorption); correlating the index of refraction with the possibility of polarizing a material (i.e., separating positive and negative charges) as expressed by a dielectric constant of the workpiece; magnetizing a workpiece (i.e., line up magnetic dipoles) as expressed by the permeability of the workpiece; or correlating a particular kind of optical absorption with the electrical conductivity of the workpiece. While the microhollow cathode discharge device may be formed in a variety of different embodiments, including the formation of a cavity in a single thick layer, in a preferred embodiment the cavity is formed through the cooperation of a plurality of thin layers fixed into a unit (e.g. firing layers or laminations of green ceramic, bonding layers of polymer, etc.). The electrical connections and circuitry can then be easily formed on various layers to make a complete device once the layers are assembled and fixed. Further, the microfluidic channel can be formed as a separate component, using any of the well known methods and material, and combined with the microhollow cathode discharge device in a convenient embodiment or it can be integrated with the microhollow cathode discharge device as described below. Examples of microfluidic channels and methods of manufacture which can be used in the presently disclosed combination can be found in the publication Angew. Chem. Int. Ed., 1998, 37, 550–575 entitled "soft lithography" by Y. Xia and G. Whitesides and related U.S. Pat. No. 6,180,239, U.S. Pat. No. 5,817,242, and PCT Patent Application designated WO 00/21659, filed Oct. 7, 1999, incorporated herein by reference.

Figure 1:
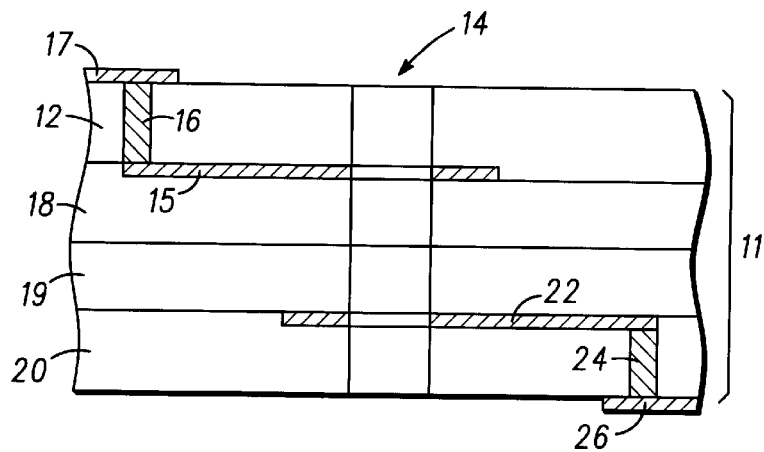
FIG. 1 is a simplified cross-sectional view of several layers of unfired ceramic forming a microhollow cathode discharge device in accordance with the present invention.

Turning now to FIG. 1, a microhollow cathode discharge device 10 is preferably formed by providing a stack 11 of layers of dielectric material, including a layer 12, in accordance with the present invention. The dielectric material forming the layers of stack 11 can be any convenient material which is capable of withstanding a plasma discharge within a microhollow cathode discharge cavity to generate a plasma based electromagnetic emission (as will be explained in more detail presently). Typical materials that can be used include ceramic, various polymeric material (e.g. PDMS or poly dimethyl sulfoxane), PMMA plus hybrid system, some materials used in the semiconductor art, etc. In the following description, for convenience, the layers are formed of green or unfired ceramic which, as explained below, is assembled and fired to form a single unit. It will be understood however, that many of the steps of formation and usage described herein can be incorporated with other materials (e.g. various polymers and some materials used in the semiconductor art) in a similar fashion.

Figure 2:
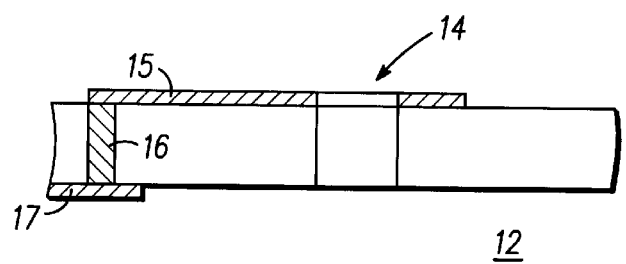
FIG. 2 is a sectional view of a single layer of green or unfired ceramic, portions thereof broken away, from the device of FIG. 1.
Figure 3:
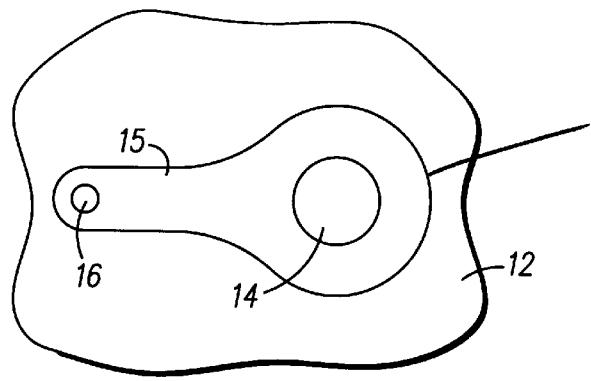
FIG. 3 is a simplified view in top plan of the layer of green or unfired ceramic of FIG. 1, portions thereof broken away.

Referring additionally to FIGS. 2 and 3, a sectional view and top plan are illustrated of single layer 12 of green or unfired ceramic material, portions thereof broken away. As understood in the art, unfired or green sheets or layers (e.g. layer 12) are formed of unfired or green ceramic material which usually includes Al$_2$O$_3$ particles, glass particles, and a binder, generally including organic material. An opening 14 is formed in layer 12 and electrical traces are include, which are formed of conductive material defining an electrode 15 surrounding opening 14 and a via 16, filled with conductive material, is connected to electrode 15. An electrical trace, defining an electrical connection 17, is formed on the reverse side of layer 12 in communication with via 16. It will be understood that the electrical traces may further include additional electrical components such as capacitors, inductors, resistors, etc. Components and electrical traces may be formed on the sheets in a variety of well known convenient methods as, for example, by screening (or the like) silver paint or other conductive material. Via 16 is filled with conductive material during the same process, by a squeegying process or the like.

In this example stack 11 includes four layers 12, 18, 19, and 20, with layer 20 being similar, but inverted, to layer 12. All of the layers include an opening axially aligned with opening 14 in layer 12, and collectively referred to hereinafter as opening 14, for convenience. Generally opening 14 is formed with a diameter in a range of at least 1 $\mu$m to preferably 100 $\mu$m and preferably allowing for up to high pressure operating conditions of about one atmosphere. Layer 20 includes electrical traces formed of conductive material defining an electrode 22 surrounding opening 14 and a via 24, filled with conductive material, connected to electrode 22. An electrical trace, defining an electrical connection 26, is formed on the reverse side of layer 20 in communication with via 24. Layer 18 may include conductive traces on the upper surface thereof which cooperate with the traces on layer 12 to enhance the thickness of electrode 42, if desired. Also, layer 19 may include conductive traces on the lower surface thereof which cooperate with the traces on layer 20 to enhance the thickness of electrode 22, if desired.

Thus, opening 14 along with the layers of conductive material (i.e. traces 15 and 22) cooperate to define a microhollow cathode discharge cavity. The microhollow cathode discharge cavity is capable of containing an environment for carrying a gas discharge within the microhollow cathode discharge cavity to generate a gas based electromagnetic wave. In a preferred embodiment, the gas discharge is a plasma discharge that generates a plasma based electromagnetic wave or emission. Here it will be understood that the terms "electromagnetic wave" or "electromagnetic emission" include ultraviolet to infrared waves or emissions, various particles (e.g. electrons, photons, phonons, etc.), and any other waves or emissions capable of being formed by the gas or plasma discharge. Electrical connections 17 and 26 are coupled to electrodes 15 and 22 for applying a cathode discharge potential to the layers of conductive material. In the example illustrated in FIG. 1, the single microhollow cathode discharge cavity is formed as a ceramic module or the like such as polymeric module, but it will be understood that an array of microhollow cathode discharge cavities could be included in a single ceramic module. In the example of an array of microhollow cathode discharge cavities, electrical traces can be included to connect the external connections for unique addressing, e.g. by row and column. This embodiment may also apply to display applications.

While a single microhollow cathode discharge cavity module is disclosed in FIG. 1, it will be understood by those skilled in the art that, for convenience in manufacturing, components of a plurality of modules are generally defined on each sheet. Also, laminated ceramic devices are generally formed using a plurality of the sheets (sometimes as many as fifty), which are stacked or positioned in overlying relationship. As is understood by those skilled in the art, the sheets are very thin (on the order of a few microns) and, generally, the total number of sheets used depends upon the circuit or circuits being integrated. During the stacking process, the sheets are vertically aligned to form common module sides and features (e.g. opening 14) through the entire stack (i.e. each module layer in a sheet overlies mating module layers in lower sheets).

After the stacking and alignment of the sheets is accomplished, the stack is pressed under a uniaxial pressure (e.g. 0–5000 psi) at an elevated temperature (e.g. 500° C. to 1500° C.) to produce bonding between adjacent sheets. As understood by those skilled in the art, the pressure and temperature must be sufficient to produce some bonding between the binders of adjacent sheets. For improvements in this bonding process see copending United States Patent Application entitled "Low-Pressure Laminated Ceramic Devices and Method", filed April 2001, bearing serial number (attorney docket number CT00-023), assigned to the same assignee, and incorporated herein by reference.

Once the stack of unfired or green ceramic sheets has been bonded together, the stack is cut or otherwise divided into individual modules. The cutting is easily accomplished since the sheets are still formed of unfired or green ceramic. The individual modules are then fired to cure the ceramic (i.e. all of the organic material is burned off and the ceramic is fused into a continuous unit). As is understood in the art, the firing temperature is generally dictated by the composition of the green ceramic material. Generally, the green ceramic material includes Al$_2$O$_3$ particles, glass particles and an organic binder. In most cases, the glass particles dictate the firing temperature, since the glass particles melt sufficiently to bind the aluminum particles together at a temperature of approximately 875° C. During the firing process, most of the organic binder is driven off to leave a ceramic comprising Al$_2$O$_3$ particles bound together by at the least partially melted and reformed glass. Also, the various sheets are bound into a virtually single structure by the firing process. In the firing process the individual modules contract or shrink approximately 13%, but the shrinkage is substantially uniform so that it does not affect the final module and the final size of features (e.g. opening 14) can be easily calculated.

Microhollow cathode discharge device 10 is capable of containing an environment for carrying a plasma discharge within the microhollow cathode discharge cavity to generate a plasma based electromagnetic emission when a cathode discharge potential is applied to electrical connections 17 and 26. In this embodiment the cavity (opening 14) is open at both ends so that a variety of environments, cathode discharge potentials, and pressures can be applied through an encompassing assembly (e.g. a larger housing, interconnecting conduits, etc.) to "tune" the cavity to various electromagnetic emissions. For example, the cavity can be tuned to change the electromagnetic emission to any desired emission in a range from infrared to ultraviolet. Also, microhollow cathode discharge device 10 can be positioned to provide the electromagnetic emissions to a separately formed microfluidic channel by positioning a portion of the channel along the axis of opening 14, by conducting the electromagnetic radiation to the channel through optical fibers or the like, or by some other conducting path.

Figure 4:
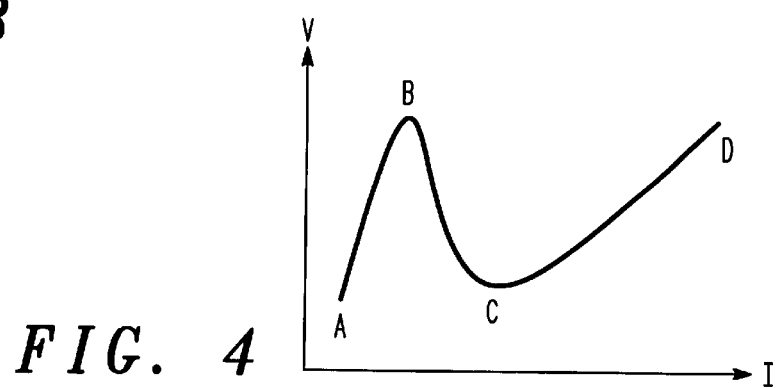
FIG. 4 is a graphic representation illustrating an IV (current versus voltage) characteristic curve for a micro hollow cathode discharge (MHCD)

Referring additionally to FIG. 4, an I-V (current versus voltage) characteristic curve is illustrated for a micro hollow cathode discharge (MHCD). As is understood by those skilled in the art, the portion of the curve between points designated A and B is known as the Townsend discharge, the portion of the curve between points designated B and C is known as the hollow cathode discharge, and the portion of the curve between points designated C and D is known as the abnormal glow discharge. The portion of interest in the present disclosure is the B-C portion. From this portion of the curve it can be seen that in a hollow cathode discharge, the current can be increased with a simultaneous drop in voltage. This phenomenon allows for an increase in energy at a lowered voltage.

Figure 5:
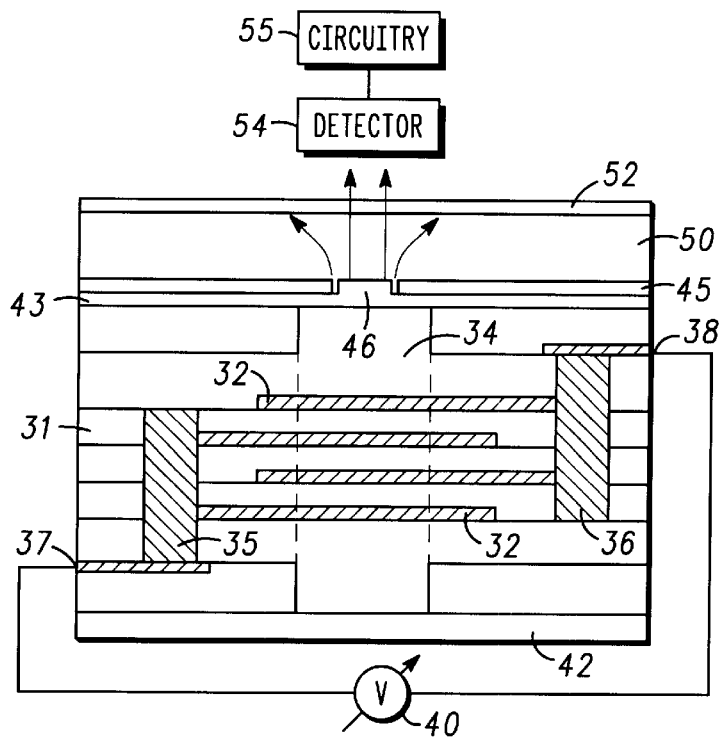
FIG. 5 is a schematic representation of an integrated microhollow cathode discharge and microfluidic device in accordance with the present invention.

Referring specifically to FIG. 5, a schematic representation is illustrated of an integrated microhollow cathode discharge and microfluidic device 30 in accordance with the present invention. Device 30 includes a dielectric body 31 with conductive layers 32 integrated therein. Body 31 and layers 32 cooperate to define a microhollow cathode discharge cavity 34 extending laterally therethrough. Conductive layers 32 are designed to extend around the periphery of cavity 34 to operate as anode and cathode electrodes and alternate layers 32 are interconnected by means of vias 35 and 36 to electrical connections 37 and 38, respectively. A power source 40 is connected between connections 37 and 38 for applying a cathode discharge potential between conductive layers 32. In this example, the lower end of cavity 34 (in FIG. 5) is sealed by means of a final layer 42 and the upper end is sealed by a transparent layer 43. A film 45 of opaque material, such as metal or the like, is applied to the surface of transparent layer 43 to define a transparent aperture 46 for the emission of electromagnetic emission out of cavity 34. In this specific example, microhollow cathode discharge cavity 34 is sealed so that it is capable of containing an environment for carrying a plasma discharge to generate a plasma based electromagnetic emission.

A microfluidic channel 50 is integrated into device 30 by forming channel 50 on or as a part of dielectric body 31. At least a portion 52 of microfluidic channel 50 is formed of material that is transparent or conducts the electromagnetic emissions so that emissions emanating from aperture 46 passes laterally through microfluidic channel 50. Thus, an electromagnetic emission path is provided extending from microhollow cathode discharge cavity 34 laterally through portion 52 of the microfluidic channel 50 to an electromagnetic emission detector 54 (e.g. a photodiode, APD, PMT, CCD array, photon counter, etc.), which may be integrated with microhollow cathode discharge cavity 34 and microfluidic channel 50. Also, electronic circuitry 55 is coupled to detector 54 for acquiring and processing data from detector 54. Electronic circuitry 55 can also be integrated into device 30 by, for example, simply fabricating detector 54 and circuitry 55 on a common semiconductor chip and mounting the chip (physically and electrically) on dielectric body 31.

By integrating microhollow cathode discharge cavity 34 and microfluidic channel 50 into a single unit, many advantages are realized including the ability to fabricate much smaller units with greater accuracy and efficiency of operation. Also, microhollow cathode discharge cavity 34 and microfluidic channel 50 can be integrated into a single unit with detector 54 to realize even greater advantages. Further, arrays of integrating microhollow cathode discharge cavities 34 (electromagnetic emission sources) can be integrated into a single unit with arrays of emission detectors and arrays of devices, such as microanalysis systems, to greatly improve the operation of such systems.

While dielectric body 31, described above, may be formed in a variety of ways using a variety of different dielectric materials, in a preferred embodiment of the present invention, dielectric body 31 is formed in laminated ceramic because of the ease of manufacturing and the ability of the ceramic to withstand the plasma, the temperatures and the pressures used. The fabrication method used is generally as described above with the addition of ceramic layer 42 to close the lower end of cavity 34 and several layers at the opposite end to define transparent aperture 46 and microfluidic channel 50. It will be understood, however, that the embodiment described is for exemplary purposes only and many changes and modifications may be incorporated.

Figure 6:
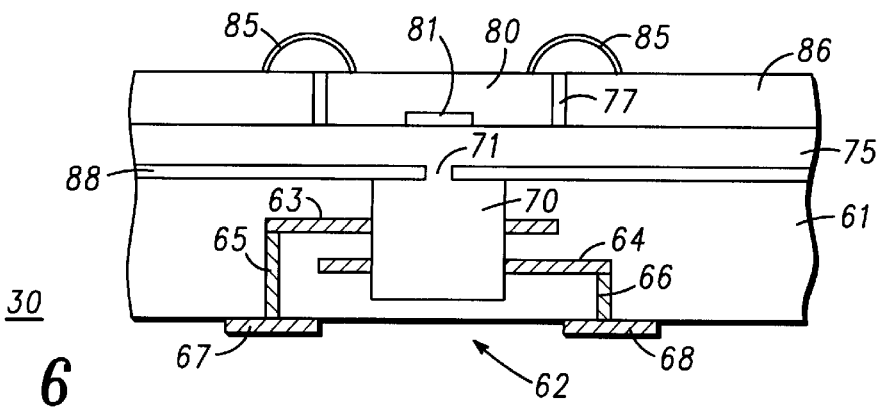
FIG. 6 is a sectional view of another integrated microhollow cathode discharge and microfluidic device in accordance with the present invention.
Figure 7:
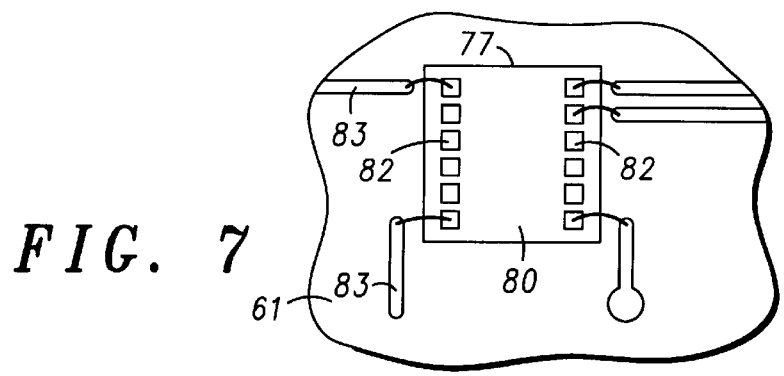
FIG. 7 is a simplified view in top plan of the device illustrated in FIG. 6.

Turning now to FIGS. 6 and 7, a sectional view and top plan, respectively, are illustrated of another integrated microhollow cathode discharge and microfluidic device 60 in accordance with the present invention. Device 60 includes a laminated ceramic body 61 with a microhollow cathode discharge cavity 62 defined therein. Microhollow cathode discharge cavity 62 includes an opening 70 with spaced apart electrodes 63 and 64 extending around the periphery, as described above. Electrodes 63 and 64 are connected by vias 65 and 66 to externally accessible connections 67 and 68, respectively. An opaque layer or coating is formed adjacent the upper end of opening 70 to define an aperture 71. A microfluidic channel 75 is formed in laminated ceramic body 61 with at least a portion of channel 75 being formed of light conductive material. It should be understood that the channel can be formed completely within the ceramic body or it can be formed as a hybrid using other materials, such as plastic, glass, silicon (semiconductor materials), polymers such as poly(dimethylsulfoxane), etc. Here the term "light" is used to denote emissions in a range of ultraviolet to infrared and "light conductive" means the material is transparent to a selected emission in that range. Microfluidic channel 75 is formed adjacent aperture 71 so that a light path is defined extending from microhollow cathode discharge cavity 62 laterally through the transparent portion of microfluidic channel 75. In this preferred embodiment, channel 75 is formed by a "soft lithography fabrication" method. More details on soft lithography can be found in an article entitled "Soft Lithography", by Y. Xia and G. Whitenides, *Angew. Chem. Int. Ed.,* 1998, 37, 550–575.

Opening 70 generally is formed with a diameter on the order of 100 $\mu$m or less, but is at least 1 $\mu$m. Stable electrical characteristics of microhollow cathode discharge cavity 62 depend on the nature and pressure of the gas (environment) within opening 70 and cathode material. Generally, microhollow cathode discharge cavities are contemplated for which Paschen's law parameters can be exploited to control the characteristics of the discharge. For example, the geometry and configuration of the electrodes of microhollow cathode discharge cavity 62 can be varied to operate with conditions such as Pd>20 Torr-mm (where P=pressure and d=distance between electrodes). In a particular arrangement, at low current and low pressure, the plasma discharge boundaries within the microhollow cathode discharge cavity are rather diffuse. The embodiment illustrated in FIG. 5, for example is essentially three microhollow cathode discharge cavities aligned in series. At high pressure (e.g. Ar) the plasma column within the cavity is more confined on the hollow cathode axis and overlapping of the three microhollow cathode discharge cavities disappears. This provides a better approach for coupling one or more microhollow cathode discharge cavities to bioassays on large planar arrays.

In this embodiment, an opening 77 is defined in the upper surface of ceramic body 61 in communication with channel 75. A semiconductor chip 80, including a light detecting diode 81 (e.g. a photodiode or the like), is positioned in opening 77 so that the light from aperture 71 in microhollow cathode discharge cavity 62 impinges on diode 81. Semiconductor chip 80 can also include electronic circuitry coupled to light detector 81 for acquiring and processing data. Semiconductor chip 80 includes bonding pads 82 for connecting diode 81 and/or any other circuitry included, to electrical traces 83 on the upper surface of ceramic body 61. Connections between bonding pads 82 and electrical traces 83 can be made, for example, by wire bonds 85, bump bonding, etc.

Microfluidic channel 75 defines I/O ports and 86 for the passage of fluids therethrough. Thus, various materials suspended in fluid can be ported through microfluidic channel 75 with light generated in microhollow cathode discharge cavity 62 being supplied through the fluid to light detector 81. Microhollow cathode discharge cavity 62 contains an environment for carrying a plasma discharge within microhollow cathode discharge cavity 62 to generate a plasma based light emission. The environment within microhollow cathode discharge cavity 32 can be selected to generate a plasma based light emission in virtually any portion of the light spectrum.

In the biotech industry, for example, the most useful spectrum is in the ultra-violet range. Here it should be noted that lasers and the like normally used in the biotech industry to produce ultra-violet light are extremely costly, large and cumbersome. However, by employing microhollow cathode discharge cavity 62 to generate a plasma based light emission such as an excimer laser assembly, light virtually anywhere in the ultraviolet range (or anywhere in the infra red to ultraviolet range) can be easily generated. Further, the potential applied to external connections 67 and 68 can be continuous, pulsed, or alternating to provide continuous or pulsed discharges.

There are several advantages to spatially locate sample-handling, fluid flow structures and detection systems on-chip to confine bio-samples in a quasi two dimensional environment, reduce reagent consumption and contamination, provide highly sensitive functional group-specific detection and testing, and possibly reduce costs. Another advantage of the present invention relates to integration of an array of light sources with multiplexing addressability when electrodes are embedded in various layers within preferably a ceramic monolithic structure. This offers unique detection systems integrated with biochip arrays for which large multiplexing is currently difficult to achieve. It is also within the scope of the invention to apply the disclosed structure and method to optoelectric and/or display technologies (e.g. optical switching, flat panel, etc.).

While we have shown and described specific embodiments of the present invention, further modifications and improvements will occur to those skilled in the art. We desire it to be understood, therefore, that this invention is not limited to the particular forms shown and we intend in the appended claims to cover all modifications that do not depart from the spirit and scope of this invention.

What is claimed is:

1. A microhollow cathode discharge and microfluidic assembly comprising:
   a dielectric body and layers of conductive material defining a microhollow cathode discharge cavity, the microhollow cathode discharge cavity capable of containing an environment for carrying a gas discharge within the microhollow cathode discharge cavity to generate a gas based electromagnetic wave;
   electrical connections coupled to the layers of conductive material for applying a cathode discharge potential to the layers of conductive material;
   a channel designed to carry a sample to be tested; and
   the electromagnetic wave being coupled to the channel for interrogating at least one physico-chemical property of a sample carried by the channel.

2. A microhollow cathode discharge and microfluidic assembly as claimed in claim 1 further including means for tuning the gas discharge within the microhollow cathode discharge cavity to change the electromagnetic wave in a range from infrared to ultraviolet.

3. A microhollow cathode discharge and microfluidic assembly as claimed in claim 1 wherein the electromagnetic wave is in the ultraviolet spectrum.

4. A microhollow cathode discharge and microfluidic assembly as claimed in claim 3 wherein the ultraviolet spectrum is coupled to radiate through a portion of the channel and the sample carried by the channel.

5. A microhollow cathode discharge and microfluidic assembly as claimed in claim 4 further including a detector mounted to receive the ultraviolet spectrum passing through the channel.

6. A microhollow cathode discharge and microfluidic assembly as claimed in claim 1 wherein the microhollow cathode discharge cavity is capable of containing an environment for carrying a plasma discharge within the microhollow cathode discharge cavity to generate a plasma based electromagnetic radiation.

7. A microhollow cathode discharge and microfluidic assembly comprising:
   a substrate;
   a dielectric body and layers of conductive material integrated on the substrate and defining a microhollow cathode discharge cavity, the microhollow cathode discharge cavity capable of containing an environment for carrying a gas discharge within the microhollow cathode discharge cavity to generate a gas based electromagnetic wave;
   electrical connections coupled to the layers of conductive material for applying a cathode discharge potential to the layers of conductive material;
   a microfluidic channel integrated on the substrate, a portion of the channel being formed of conductive material for conducting the electromagnetic wave; and
   an electromagnetic path extending from the microhollow cathode discharge cavity laterally through the portion of the microfluidic channel.

8. A microhollow cathode discharge and microfluidic assembly as claimed in claim 7 including in addition an electromagnetic detector positioned to receive electromagnetic waves from the path passing through the portion of the microfluidic channel.

9. A microhollow cathode discharge and microfluidic assembly as claimed in claim 8 wherein the electromagnetic detector is integrated on the substrate.

10. A microhollow cathode discharge and microfluidic assembly as claimed in claim 8 further including electronic circuitry coupled to the electromagnetic detector for acquiring and processing data.

11. A microhollow cathode discharge and microfluidic assembly as claimed in claim 10 wherein the electronic circuitry is integrated on the substrate.

12. A microhollow cathode discharge and microfluidic assembly as claimed in claim 7 wherein the dielectric body includes a plurality of layers of dielectric material interleaved with the layers of conductive material and integrated on the substrate, the layers of dielectric material and the layers of conductive material having an opening extending therethrough defining the microhollow cathode discharge cavity.

13. A microhollow cathode discharge and microfluidic assembly as claimed in claim 12 wherein the layers of dielectric material include laminated ceramic material.

14. A microhollow cathode discharge and microfluidic assembly as claimed in claim 12 wherein the layers of dielectric material include laminated polymer material.

15. A microhollow cathode discharge and microfluidic assembly as claimed in claim 13 wherein the microfluidic channel is formed in one or more layers of the laminated ceramic material adjacent one end of the microhollow cathode discharge cavity.

16. A microhollow cathode discharge and microfluidic assembly as claimed in claim 7 wherein the dielectric body and layers of conductive material define a plurality of spaced apart microhollow cathode discharge cavities integrated on the substrate.

17. A microhollow cathode discharge and microfluidic assembly as claimed in claim 16 including a plurality of microfluidic channels integrated on the substrate, and an electromagnetic path extending from each of the plurality of microhollow cathode discharge cavities laterally through portions of the plurality of microfluidic channels.

18. A microhollow cathode discharge and microfluidic assembly as claimed in claim 16 wherein the electrical connections are coupled to the layers of conductive material for applying a cathode discharge potential to selected microhollow cathode discharge cavities of the plurality of spaced apart microhollow cathode discharge cavities.

19. A microhollow cathode discharge and microfluidic assembly as claimed in claim 7 further including means for tuning the plasma discharge within the microhollow cathode discharge cavity to change the electromagnetic wave in a range from infrared to ultraviolet.

20. A microhollow cathode discharge and microfluidic assembly as claimed in claim 7 having an environment within the microhollow cathode discharge cavity including material selected to produce ultra-violet light.

21. A microhollow cathode discharge and microfluidic assembly as claimed in claim 20 wherein the material selected includes excimer molecules.

22. A microhollow cathode discharge and microfluidic assembly as claimed in claim 7 wherein the microhollow cathode discharge cavity has dimensions selected to generate a lasing cavity.

23. A microhollow cathode discharge and microfluidic assembly as claimed in claim 22 wherein the lasing cavity has an environment therein including material including excimer molecules selected to produce ultra-violet light.

24. A microhollow cathode discharge and microfluidic assembly as claimed in claim 7 wherein the electrical connections are coupled to a source of power designed to produce a continuous discharge in the microhollow cathode discharge cavity.

25. A microhollow cathode discharge and microfluidic assembly as claimed in claim 7 wherein the electrical connections are coupled to a source of power designed to produce a pulsed discharge in the microhollow cathode discharge cavity.

26. A microhollow cathode discharge and microfluidic assembly comprising:
a plurality of layers of ceramic material each having an opening extending therethrough, at least some of the plurality of layers having conductive material thereon defining electrodes surrounding the opening and vias filled with conductive material connected to the electrodes, two layers of the plurality of layers further having conductive material extending to form an external contact, the plurality of layers being fired into an integral ceramic unit defining a microhollow cathode discharge cavity with spaced apart and interconnected electrodes and electrical connections coupled to the electrodes for applying a cathode discharge potential to the electrodes;
an environment capable of carrying a gas discharge within the microhollow cathode discharge cavity to generate a gas based electromagnetic wave;
a microfluidic channel integrated with the integral ceramic unit, a portion of the channel being formed of conductive material for conducting the electromagnetic wave from the cavity; and
an electromagnetic path extending from the microhollow cathode discharge cavity laterally through the portion of the microfluidic channel.

27. A microhollow cathode discharge and microfluidic assembly as claimed in claim 26 wherein the integral ceramic unit is a monolithic three dimensional unit.

28. A microhollow cathode discharge and microfluidic assembly as claimed in claim 27 including in addition an electromagnetic detector positioned to receive electromagnetic waves from the electromagnetic path passing through the portion of the microfluidic channel.

29. A microhollow cathode discharge and microfluidic assembly as claimed in claim 28 wherein the electromagnetic detector is integrated with the integral ceramic unit.

30. A microhollow cathode discharge and microfluidic assembly as claimed in claim 28 further including electronic circuitry coupled to the electromagnetic detector for acquiring and processing data.

31. A microhollow cathode discharge and microfluidic assembly as claimed in claim 30 wherein the electronic circuitry is integrated with the integral ceramic unit.

32. A microhollow cathode discharge and microfluidic assembly as claimed in claim 26 wherein the integral ceramic unit defines a plurality of spaced apart microhollow cathode discharge cavities.

33. A microhollow cathode discharge and microfluidic assembly as claimed in claim 32 including a plurality of microfluidic channels integrated with the integral ceramic unit, and an electromagnetic path extending from each of the plurality of microhollow cathode discharge cavities laterally through portions of the plurality of microfluidic channels.

34. A microhollow cathode discharge and microfluidic assembly as claimed in claim 32 wherein the electrical connections are coupled to the electrodes for applying a cathode discharge potential to selected microhollow cathode discharge cavities of the plurality of spaced apart microhollow cathode discharge cavities.

35. A method of fabricating a microhollow cathode discharge and microfluidic assembly comprising the steps of:
providing a plurality of layers of dielectric material each having an opening extending therethrough, at least some of the plurality of layers having conductive material thereon defining electrodes surrounding the opening and conductive material extending to form electrical contacts;
fixing the plurality of layers of material together in overlying relationship to form a stack with the openings aligned, the stack defining a microhollow cathode discharge cavity with spaced apart and interconnected electrodes and electrical connections coupled to the electrodes for applying a cathode discharge potential to the electrodes, the microhollow cathode discharge cavity being capable of containing an environment for carrying a gas discharge within the microhollow cathode discharge cavity to generate a gas based electromagnetic wave;

providing a channel designed to carry a sample to be interrogated; and coupling the electromagnetic emission to the channel for interrogating at least one physico-chemical property of a sample carried by the channel.

36. A method of fabricating a microhollow cathode discharge and microfluidic assembly as claimed in claim 35 wherein the layers of dielectric material include laminated ceramic material.

37. A method of fabricating a microhollow cathode discharge and microfluidic assembly as claimed in claim 35 wherein the layers of dielectric material include laminated polymer material.

38. A method of fabricating an integrated microhollow cathode discharge and microfluidic assembly as claimed in claim 35 including a step of tuning the gas discharge within the microhollow cathode discharge cavity to change the electromagnetic wave in a range from infrared to ultraviolet.

39. A method of fabricating an integrated microhollow cathode discharge and microfluidic assembly as claimed in claim 35 wherein the step of providing the channel includes defining a hybrid unit including a channel and a microhollow cathode discharge cavity using one of ceramic, plastic, glass, silicon and polymer.

40. A method of fabricating an integrated microhollow cathode discharge and microfluidic assembly as claimed in claim 35 wherein the step of providing the channel includes forming a channel in the plurality of layers of dielectric material using soft lithography fabrication.

41. A method of fabricating a microhollow cathode discharge and microfluidic assembly comprising the steps of:

providing a plurality of layers of unfired ceramic material each having an opening extending therethrough, at least some of the plurality of layers having conductive material thereon defining electrodes surrounding the opening and vias filled with conductive material connected to the electrodes, two layers of the plurality of layers further having conductive material extending to form electrical contacts;

stacking the plurality of layers of unfired ceramic material in overlying relationship to form a stack with the openings aligned;

heating and applying a pressure to the stack to fixedly bond the plurality of layers in the stack together;

firing the stack to cure the plurality of layers of unfired ceramic material into an integral ceramic unit defining a microhollow cathode discharge cavity with spaced apart and interconnected electrodes and electrical connections coupled to the electrodes for applying a cathode discharge potential to the electrodes;

integrating a microfluidic channel with the integral ceramic unit, a portion of the channel being formed of conductive material for electromagnetic emissions; and providing an electromagnetic emissions path extending from the microhollow cathode discharge cavity laterally through the portion of the microfluidic channel.

42. A method of fabricating a microhollow cathode discharge and microfluidic assembly as claimed in claim 41 wherein the step of integrating the microfluidic channel with the integral ceramic unit includes a step of forming the microfluidic channel in the plurality of layers of unfired ceramic material.

43. A method of fabricating a microhollow cathode discharge and microfluidic assembly as claimed in claim 42 wherein the step of providing the electromagnetic path extending from the microhollow cathode discharge cavity laterally through the portion of the microfluidic channel includes providing a electromagnetic path in the plurality of layers of unfired ceramic material.

44. A method of fabricating a microhollow cathode discharge and microfluidic assembly as claimed in claim 41 including a step of providing an environment capable of carrying a gas discharge within the microhollow cathode discharge cavity to generate a gas based electromagnetic wave.

45. A method of fabricating an integrated microhollow cathode discharge and microfluidic assembly as claimed in claim 41 including a step of positioning an electromagnetic detector to receive electromagnetic waves from the electromagnetic path passing through the portion of the microfluidic channel.

46. A method of fabricating an integrated microhollow cathode discharge and microfluidic assembly as claimed in claim 45 including a step of coupling electronic circuitry to the electromagnetic detector for acquiring and processing data.

47. A method of fabricating an integrated microhollow cathode discharge and microfluidic assembly as claimed in claim 45 wherein the step of positioning the electromagnetic detector includes integrating the electromagnetic detector on a common substrate with the microhollow cathode discharge cavity and the microfluidic channel.

48. A method of fabricating an integrated microhollow cathode discharge and microfluidic assembly as claimed in claim 41 including a step of tuning the gas discharge within the microhollow cathode discharge cavity to change the electromagnetic wave in a range from infrared to ultraviolet.

49. A method of fabricating an integrated microhollow cathode discharge and microfluidic assembly as claimed in claim 41 wherein the step of integrating the microfluidic channel includes defining a hybrid unit including a channel and a microhollow cathode discharge cavity using one of ceramic, plastic, glass, silicon and polymer.

50. A method of fabricating an integrated microhollow cathode discharge and microfluidic assembly as claimed in claim 41 wherein the step of integrating the microfluidic channel includes forming a channel in the layers of unfired ceramic material using soft lithography fabrication.

51. A method of utilizing a microhollow cathode discharge and microfluidic assembly comprising the steps of:

providing a microhollow cathode discharge cavity with spaced apart and interconnected electrodes and electrical connections coupled to the electrodes for applying a cathode discharge potential to the electrodes, the microhollow cathode discharge cavity being capable of containing an environment for carrying a gas discharge within the microhollow cathode discharge cavity to generate a gas based electromagnetic wave;

providing a channel designed to carry a sample to be interrogated; and coupling the electromagnetic emission to the channel for interrogating at least one physico-chemical property of a sample carried by the channel.

52. A method of utilizing an integrated microhollow cathode discharge and microfluidic assembly as claimed in claim 51 including a step of tuning the gas discharge within the microhollow cathode discharge cavity to change the electromagnetic wave in a range from infrared to ultraviolet.

* * * * *